(12) United States Patent
Morton

(10) Patent No.: US 6,764,473 B2
(45) Date of Patent: *Jul. 20, 2004

(54) OSTOMY APPLIANCE WITH INTEGRAL CLOSURE

(76) Inventor: Jesse R. Morton, 5700 Luxemburg St. #305, Rockville, MD (US) 20852

( * ) Notice: Subject to any disclaimer, the term of this patent is extended or adjusted under 35 U.S.C. 154(b) by 0 days.

This patent is subject to a terminal disclaimer.

(21) Appl. No.: 10/347,285

(22) Filed: Jan. 21, 2003

(65) Prior Publication Data

US 2003/0109838 A1 Jun. 12, 2003

Related U.S. Application Data

(63) Continuation-in-part of application No. 09/893,534, filed on Jun. 29, 2001.
(60) Provisional application No. 60/218,778, filed on Jul. 18, 2000.

(51) Int. Cl.$^7$ .................................................. A61F 5/44
(52) U.S. Cl. ................. 604/334; 604/317; 604/332; 604/333; 604/335; 604/336; 604/337; 604/338; 604/339; 604/340; 604/341; 604/342
(58) Field of Search .............................. 604/332, 333, 604/334, 335, 336, 337, 338, 339, 340, 341, 342

(56) References Cited

U.S. PATENT DOCUMENTS

| | | | | |
|---|---|---|---|---|
| 3,385,298 A | * | 5/1968 | Fenton | 604/332 |
| 3,523,534 A | * | 8/1970 | Nolan | 604/335 |
| 3,690,320 A | * | 9/1972 | Riely | 604/333 |
| 3,825,005 A | * | 7/1974 | Fenton | 604/335 |
| 4,367,742 A | * | 1/1983 | Ornstein | 604/333 |
| 4,403,991 A | * | 9/1983 | Hill | 604/337 |
| 4,460,359 A | * | 7/1984 | Fenton | 604/277 |
| 4,465,486 A | * | 8/1984 | Hill | 604/337 |
| 4,551,888 A | * | 11/1985 | Beecher | 24/30.5 P |
| 4,561,858 A | * | 12/1985 | Allen et al. | 604/336 |
| 4,755,177 A | * | 7/1988 | Hill | 604/336 |
| 4,983,172 A | * | 1/1991 | Steer et al. | 604/332 |
| 4,988,343 A | * | 1/1991 | Ballan | 604/332 |
| 5,050,272 A | * | 9/1991 | Robinson et al. | 24/30.5 R |
| 5,125,133 A | * | 6/1992 | Morrison | 24/30.5 R |
| 5,403,094 A | | 4/1995 | Tomic | 383/63 |
| 5,617,616 A | * | 4/1997 | Cutts, Sr. | 24/30.5 R |
| 5,690,623 A | | 11/1997 | Lenz et al. | 604/333 |
| 5,843,054 A | * | 12/1998 | Honig | 604/345 |
| 5,950,285 A | | 9/1999 | Porchia et al. | 24/400 |
| 5,968,023 A | * | 10/1999 | Olsen | 604/334 |
| 6,231,553 B1 | * | 5/2001 | Hulett | 604/333 |

FOREIGN PATENT DOCUMENTS

GB      2 268 065 A  *  5/1994  ............. A61F/5/44

OTHER PUBLICATIONS

UOA Facts and Figures by Mary Jane Wolfe via Ostomy Association of Boston, Mar./Apr. 1999.

* cited by examiner

Primary Examiner—Henry Bennett
Assistant Examiner—Nihir Patel
(74) Attorney, Agent, or Firm—Arent Fox PLLC

(57) ABSTRACT

An ostomy pouch for both one and two-piece ostomy appliances having an integral closure at the bottom of the pouch to allow the pouch to be emptied and re-sealed without the use of a separate closure. The integral closure has mating parts that are locked together and provides the ostomy appliance with a leak-proof, odor-proof seal when in a closed, sealed, and locked position. A slider, when the appliance is closed, can be moved along the integral closure, thereby separating the mated male and female parts to provide an opening through which the stored contents within the ostomy pouch can be emptied. After the stored contents have been emptied, the slider can reseal the pouch by rejoining the male and female parts. The integral closure is manufactured from material that is different and more rigid than the material used to manufacture the ostomy pouch.

31 Claims, 5 Drawing Sheets

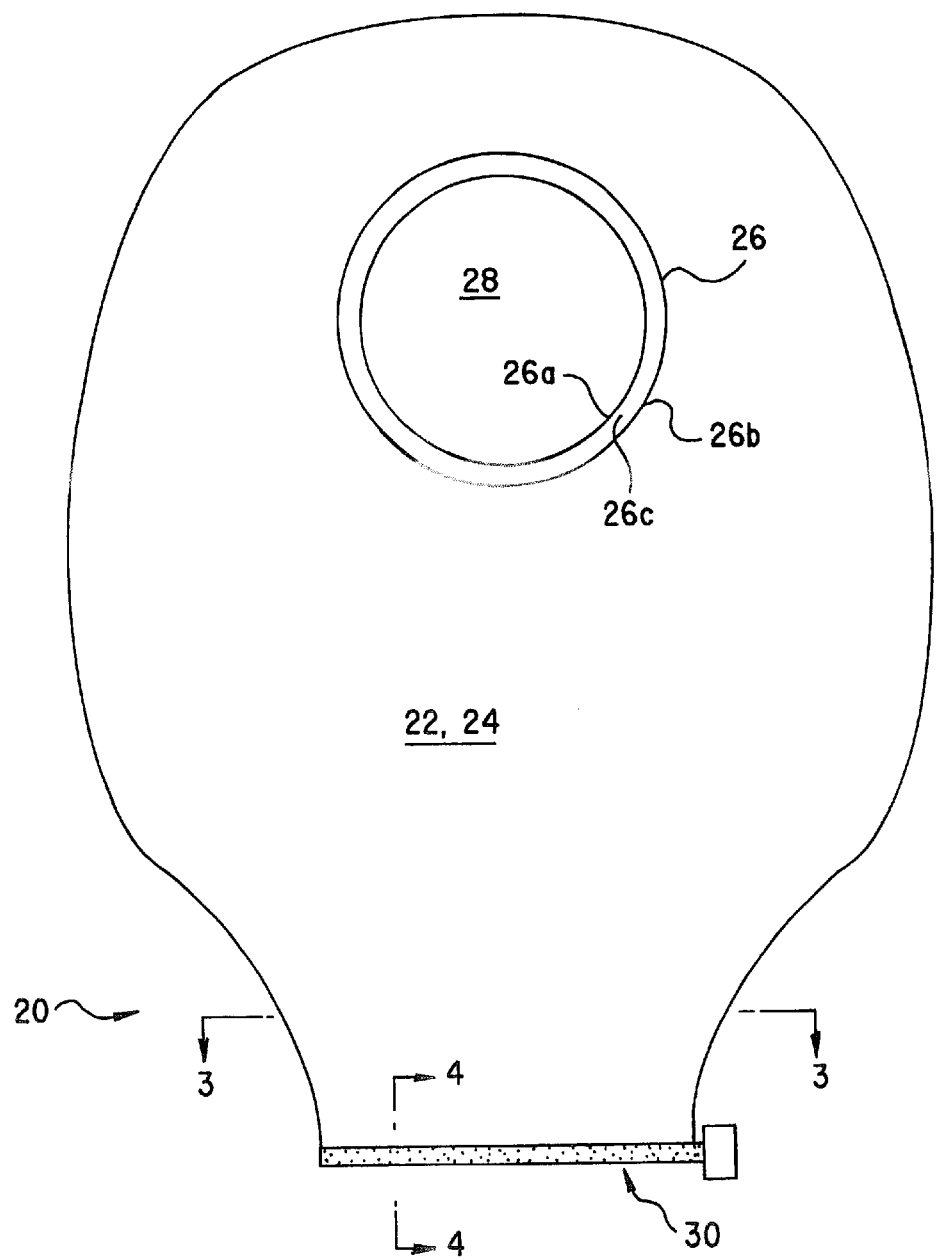

OSTOMY APPLIANCE WITH INTEGRAL CLOSURE

CROSS-REFERENCE TO RELATED APPLICATION

This application is a continuation-in-part of application Ser. No. 09/893,534, filed Jun. 29, 2001, which is now U.S. Pat. No. 6,544,241, and which claim the benefit of U.S. Provisional Application No. 60/218,778, filed Jul. 18, 2000. The disclosures of the prior applications are hereby incorporated by reference herein in their entirety.

BACKGROUND OF THE INVENTION

An ostomy is a surgical operation in which the flow of either the colon or small intestine, hereinafter the intestine, of the patient, hereinafter referred to as the ostomate, is redirected from the normal passageway and replaced with a portion of the intestine protruding from an orifice surgically formed in the abdomen. The portion of the intestine protruding from the surgically formed orifice is commonly referred to as a stoma in the medical community. The contents, i.e., fecal matter, of the intestine are then involuntarily discharged through the surgically formed orifice and collected by an ostomy appliance positioned over the stoma and attached to the abdomen of the ostomate.

An ostomy appliance conventionally includes a wafer and an ostomy pouch. The ostomy appliance may either be a one piece device or a two piece device, each of which includes a separate closure device to seal the bottom of the ostomy pouch. In the two piece device, the wafer is separate from the ostomy pouch and attached to the body of the ostomate. With the one piece device, the wafer is integral with the ostomy pouch. Regardless of whether the wafer is separate from or integral with the ostomy pouch, the wafer is positioned to be proximate the orifice surgically formed in the abdomen.

The wafer includes a flexible piece of synthetic material that adheres to the abdomen on a body side of the wafer and has an opening formed near the center thereof for the stoma to pass therethrough. The other side of the wafer includes a locking ring designed to engage the ostomy pouch, the locking ring encompassing the opening formed near the center of the wafer.

The ostomy pouch is used to collect the fecal matter discharged from the stoma through the opening in the wafer. The pouch is known to be formed from a synthetic material, such as rubber or plastic, and comprises two wall panels joined together along the top and both sides. One of the wall panels, that is, the wall panel closest to the abdomen of the ostomate, has an opening formed therein that also includes a locking ring configured to correspond to and lockingly mate with the locking ring of the wafer.

The opening and locking ring of the wall panel of the ostomy pouch closest to the abdomen of the ostomate is placed around the stoma and either attached directly to the body of the ostomate or to the wafer. The above-described arrangement results in the stoma being completely enclosed and sealed by the ostomy pouch and wafer. When the ostomy appliance is applied correctly to the ostomate, the ostomy pouch and wafer, in conjunction with a closure, permit the stoma to be completely enclosed, providing an air-tight, leak-proof, odor-proof seal. The closure is described in further detail below. In use, the ostomy pouch collects the fecal matter discharged from the stoma. When necessary, the ostomy pouch is then emptied of the collected contents.

Currently, there are two methods used by ostomates to empty the contents of the ostomy pouch. The first method used by ostomates includes a disposable ostomy pouch, which requires the ostomate to simply remove, discard and replace the entire ostomy pouch with a clean and empty disposable ostomy pouch. This type of ostomy pouch is commonly referred to as a non-drainable or single use device. Obviously, this method can become quite costly to the ostomate as well as the insurance provider, if there is one.

The second method, which is the more preferable and commonly used method as it is more cost effective and convenient, is to discharge the contents from the bottom of the open ended ostomy pouch. The opening is then closed via the separate closure and the ostomy pouch reused. This type of ostomy pouch is commonly referred to as a drainable or multi use device.

There are several well known manners for sealing the opening formed in the bottom of the ostomy pouch. For example, U.S. Pat. Nos. 4,755,177 and 5,125,133 disclose the use of a folding bar and clamp, respectively, to seal the bottom opening of the ostomy pouch after the contents have been emptied. Because the ostomy appliance is worn by the ostomates at all times of the day, whatever manner is used to seal the bottom opening of the ostomy pouch closed, it is imperative for health, safety, and quality of life reasons that the closure be secure and tight, so as to permit the normal twisting, turning, and other such active motions performed by individuals during typical daily life. As such, there must be zero, or very little, risk in the closure becoming separated or broken, which would result in the unintentional release of the contents in the ostomy pouch.

There have been several attempts to solve the above-described problem of the bottom opening of the ostomy pouch from unintentionally opening and provide a secure, fluid and air-tight seal when normally closed. However, each of the currently used closure techniques have particular disadvantages. Such disadvantages include techniques that are complicated to perform, folding bars and clamps that are difficult and costly to manufacture, the inability to properly seal the bottom opening of the ostomy pouch, the inability to of the ostomate to empty the full ostomy pouch without contacting the fecal matter contained therein, the inability of the ostomate to be comfortable enough to allow for normal daily activities, the inability to properly use the ostomy pouch due to the limited dexterity of the ostomates because of, for example, their advanced age, and danger of losing or dropping the clamp.

There are several drawbacks associated with the disposable ostomy pouches. For example, it is fairly well established in the medical community that disposable ostomy pouches are feasible only with colostomy ostomates because of the frequency of emptying the contents. In particular, while colostomy ostomates generally discard the pouch approximately once a day, illeostomy ostomates empty the contents of the pouches on average 5 times, or more, per day. As such, illeostomy ostomates have to replace the disposable pouches at least five times a day. Since ostomy pouches are costly, the use and disposal of several pouches per day is economically impractical. Although the frequency of colostomy ostomates having to dispose such pouches is less than illeostomy ostomates, even having to replace the pouches once a day can become costly. Additionally, unlike reusable ostomy pouches where only the contents are discarded, disposable pouches must be discarded in its entirety, thus not permitting disposal in a toilet. Rather, the disposable pouches, with the contents therein, must be disposed in a sealed receptacle bin in order to avoid the offensive odors associated with such and maintain cleanliness. Moreover, ostomates that use the disposable pouch encounter the problem of the replacement pouches not being compatible with the type of wafer already being used by the ostomate, in addition to the inconvenience of having to carry several replacement pouches with them at all times.

As mentioned above, currently, the more popular manner of sealing the bottom opening of the ostomy pouch is the clamp similar to that disclosed in U.S. Pat. No. 5,125,133. As briefly explained above, there are several drawbacks to using the clamp as well as the aforementioned folding bar. For example, the United Ostomy Association has published reports indicating the average age of ostomates is 73 with 64% of all ostomates being in the 65–90 age group. Put simply, a majority, but nowhere near all, of ostomates are elderly.

Therefore, the typical ostomate is very likely to have limited dexterity. Typically, the use of a clamp requires the ostomate, to first sit on the toilet, place the ostomy pouch between his or her legs, lift the ostomy pouch with one hand so the contents are not placing pressure on the bottom opening that is sealed by the clamp, release the clamp with the other hand by pinching a small release mechanism on the clamp, separate the clamp closure, place the clamp on a separate surface while still holding the ostomy pouch with one hand, then slowly placing the now unsealed ostomy pouch above an uncovered toilet, and release the contents of the ostomy pouch. As if the above-detailed process is not labor intensive enough, once the contents of the ostomy pouch have been disposed of in the toilet, the ostomate must then clean the inside of the ostomy pouch as thoroughly as possible. The bottom opening of the pouch must then be sealed with the clamp while making sure the clamp is attached properly and securely, without dropping the clamp in to the toilet.

Consequently, the above-described method is extremely tedious, difficult, and extraordinarily risky for ostomates with limited dexterity, let alone average dexterity. Therefore, the likelihood of the contents being unintentionally evacuated prematurely, disposed incorrectly, or even have the clamp fall into the toilet, along with numerous other undesirable effects, is an everyday concern for every ostomate.

Another drawback with using the clamp or folding bar to seal the bottom opening of the ostomy pouch is that fecal matter may come in contact not only with the inside lining of the pouch, but also, when emptying the contents therein, with a portion of the exterior of the ostomy pouch. Additionally, when the ostomate is emptying the contents of the ostomy pouch, since the fecal matter is evacuated through the bottom opening of the ostomy pouch, the entire opening is contaminated. Accordingly, an ostomate must then properly clean each portion of the ostomy pouch, including the opening, that has come in contact with the fecal matter.

Cleaning the contaminated portions of the ostomy pouch requires at the very least a separate piece of toilet paper, or the like, to properly clean the portion of the ostomy pouch. The clamp or folding bar is then placed back on the bottom portion of the ostomy pouch, leaving a section of the bottom of the pouch that is to be folded up into the clamp or folding bar exposed. As the remaining portion has most likely been contacted and thereby contaminated by the fecal matter, the ostomate needs to clean, as well as possible, the lining at the bottom of the ostomy pouch, the ostomate must endure the fact that the exposed lining has most likely not been thoroughly cleaned, and the ostomate must also endure the lingering odors associated with the contents of the ostomy pouch.

Yet another drawback to the clamp is the lack of comfort it provides the ostomate to enjoy routine daily activities. In particular, the clamps currently being used are made of a hard, non-durable, synthetic plastic. Although the clamp typically has a slight curved shape allegedly for the comfort of the ostomate, the fact remains the hard plastic is extremely uncomfortable, and poses several dangers when the ostomate engages in any sort of activity or recreational sport like walking jogging, and the like. Since the hard plastic clamp is not fixedly attached to the body of the ostomate, the clamp moves around substantially during such activities and has been known to gouge the thigh or pelvic region of the ostomate causing discomfort, and in extreme cases requiring medical attention.

The clamps are also costly to manufacture. In other words, the use of a separate component with the ostomy appliance, i.e., the clamp or folding bar, requires the manufacture of a separate piece besides the wafer and ostomy pouch. Manufacturers require otherwise unnecessary machines, materials, and laborers, not to mention costs associated with research and development, to make the clamps that are commonly provided to ostomates at no charge.

U.S. Pat. No. 3,825,005 attempts to avoid the above-described drawbacks by providing a reusable pouch having the closure attached to the pouch. However, the reusable pouch does not successfully overcome the drawbacks associated with complicated use, expensive manufacturing costs, and provide a tight seal as is necessary to securely hold the fecal matter. The reusable pouch has several parts that are complicated to use, difficult to manufacture, and requires a similar method of use as with the above-described clamp in terms of emptying the contents of the pouch.

Furthermore, the reusable pouch has several folds that require a complicated method of sealing in light of the numerous components. More importantly, the reusable pouch does not appear to overcome the cleanliness issue involved with emptying the reusable pouch, and if anything appears to make cleaning of the interior of the pouch more complicated and difficult. Additionally, the method for closing the reusable pouch is not secure.

As such, currently there exists a need for a convenient, and cost effective ostomy appliance that overcomes all of the prior mentioned drawbacks of known ostomy appliances.

SUMMARY OF THE INVENTION

It is an object of this invention to overcome the above-described drawbacks.

It is also an object of this invention to provide a clean, easy-to-use, cost efficient, secure, and unrestricting ostomy pouch having an integral closure for ostomates.

It is yet another object of this invention to provide a reusable, resealable ostomy pouch that can be emptied without being detached from the abdomen of the ostomate, and without the need of a clamp, folding bar, or other such securing device that is separate from the ostomy pouch. The ostomy pouch of this invention includes a closure that is integral with the ostomy pouch. The integral closure is a sealing mechanism that includes a male portion formed on a first wall panel of the ostomy pouch at the bottom opening and a female portion formed on the second wall panel of the ostomy pouch at the bottom opening. The male and female portions are configured to lockingly mate with each other either by manual pressure, that is, finger pressure, or with a slider mechanism. The sliding mechanism joins the male and female portions so the bottom opening is closed to provide a secure seal.

The first and second wall panels of the ostomy pouch are formed from a plastic, thermoplastic, or other such reusable, gas and liquid impermeable material. Such materials include, but are not limited to, a polymeric material, such as polyethylene, copolymer of vinyl chloride, or polyvinylidene chloride; and laminates such as ethylene vinylacetate or polyvinylidene chloride, wherein the polymeric material may be either clear or opaque.

More example of the gas and liquid permeable materials include, a low density polyethylene, linear low density polyethylene, substantially linear copolymers of ethylene and a C3–C8 α-olefin, polypropylene, polyvinyl chloride, mixtures of two or more of the above-listed polymers, or mixtures with one or more of the above-listed polymers with another thermoplastic polymer Another example of a gas and liquid impermeable material includes a polyolefin film laminated with an appropriate barrier material, such as a low density polyethylene coextruded with a layer of polyvinylidene chloride.

The thickness of such liquid and gas impermeable liquid materials will vary depending on the particular polymeric material used, but is usually in the range of approximately 2 to 8 mils.

Also, the outer surfaces of one or both of the first and second wall panels may be provided with a relatively soft breathable fabric covering layer to enhance wearer comfort and prevent the outer surfaces of the first and second wall panels from adhering to the skin or clothing of the ostomate. Such a soft covering layer may be formed from a soft, non-woven thermoplastic material or a woven material, such as, for example, cotton.

The first and second portions, along with the slider mechanism, of the integral closure are formed from a material that is different from and more rigid than the material from which the first and second wall panels are formed. The more rigid material of the integral closure increases the lock strength of the integral closure because such materials typically do not give as easily as the relatively less rigid materials from which the first and second wall panels are formed, thereby making it more difficult for the integral closure to disengage from a locked state and prevent unintentional discharge of the contents of the ostomy pouch. Examples of such stiffer materials are, but not limited to, nylon, polypropylene, polystyrene, acetal, toughened acetal, polyketone, polybutylene terephthalene, high density polyethylene, polycarbonate, or ABS. Furthermore, the first portion, the second portion, as well as the slider, can be manufactured using any well known method, such as, for example, blow or cast extrusion, as well as injection molding.

These and other objects of the invention will be described in or be apparent from the following description of specific embodiments.

BRIEF DESCRIPTION OF THE DRAWINGS

The invention will be described in conjunction with the following drawings in which like reference numerals designate like elements and wherein:

FIG. 2A is the ostomy pouch with the integral closure according to a preferred embodiment of this invention;

DETAILED DESCRIPTION OF PREFERRED EMBODIMENTS

Figure 1:
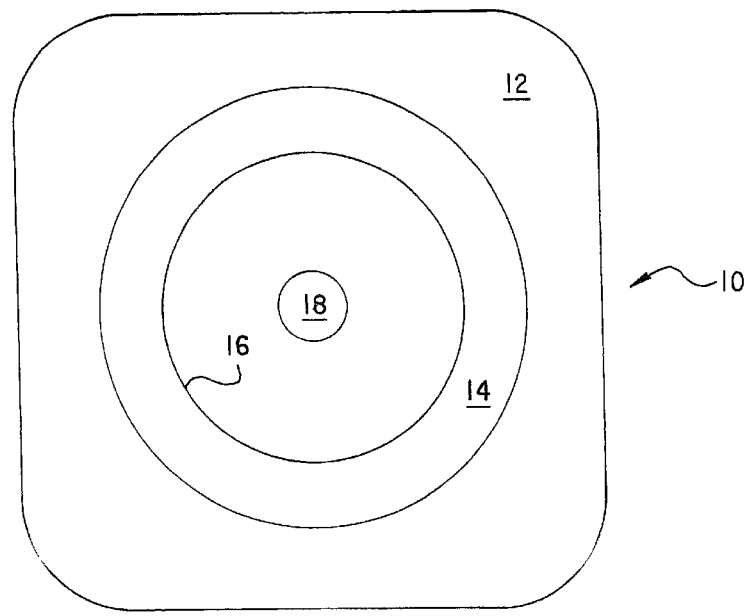
FIG. 1 is a perspective view of a wafer used with the ostomy pouch according to an embodiment of this invention.

FIG. 1 is a perspective view of the wafer 10 used with the ostomy pouch 20 according to this invention. The wafer 10 includes a skin layer 12 and semi rigid disk 14 attached to the skin layer 12. The skin layer 12 is made of a suitable flexible material and has an adhesive on the back side of the skin layer so that the wafer 10 adheres to the skin of the ostomate. The disk 14 is disposed substantially in the center of the skin layer 12 and includes a locking ring 16 and a stoma opening 18. The locking ring 16 projects away from the skin layer 12 and disk 14 and locks with a corresponding locking ring 26 on the ostomy pouch 20 as will be explained in further detail below. Furthermore, the stoma opening 18 is configured to permit the stoma to pass therethrough.

Although the skin layer 12 is shown as being rectangular and the disk 14, locking ring 16 and stoma opening 18 are shown as being circular in shape, respectively, it should be understood that the shown shapes are merely for illustrative purposes and it is within the scope of this invention to have the components be any suitable geometric shape.

Figure 3A:
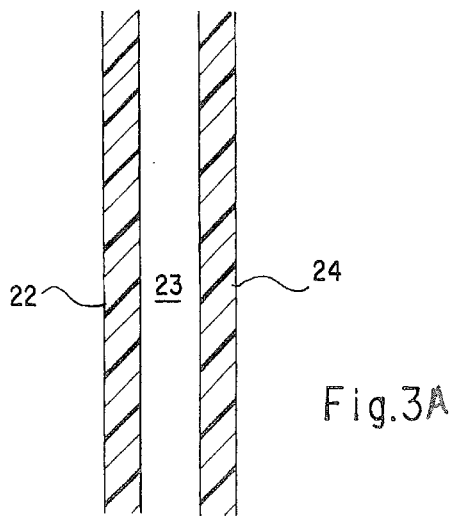
FIG. 3A is a cross-sectional view of the ostomy pouch shown in FIGS. 2A and 2B.
Figure 2B:
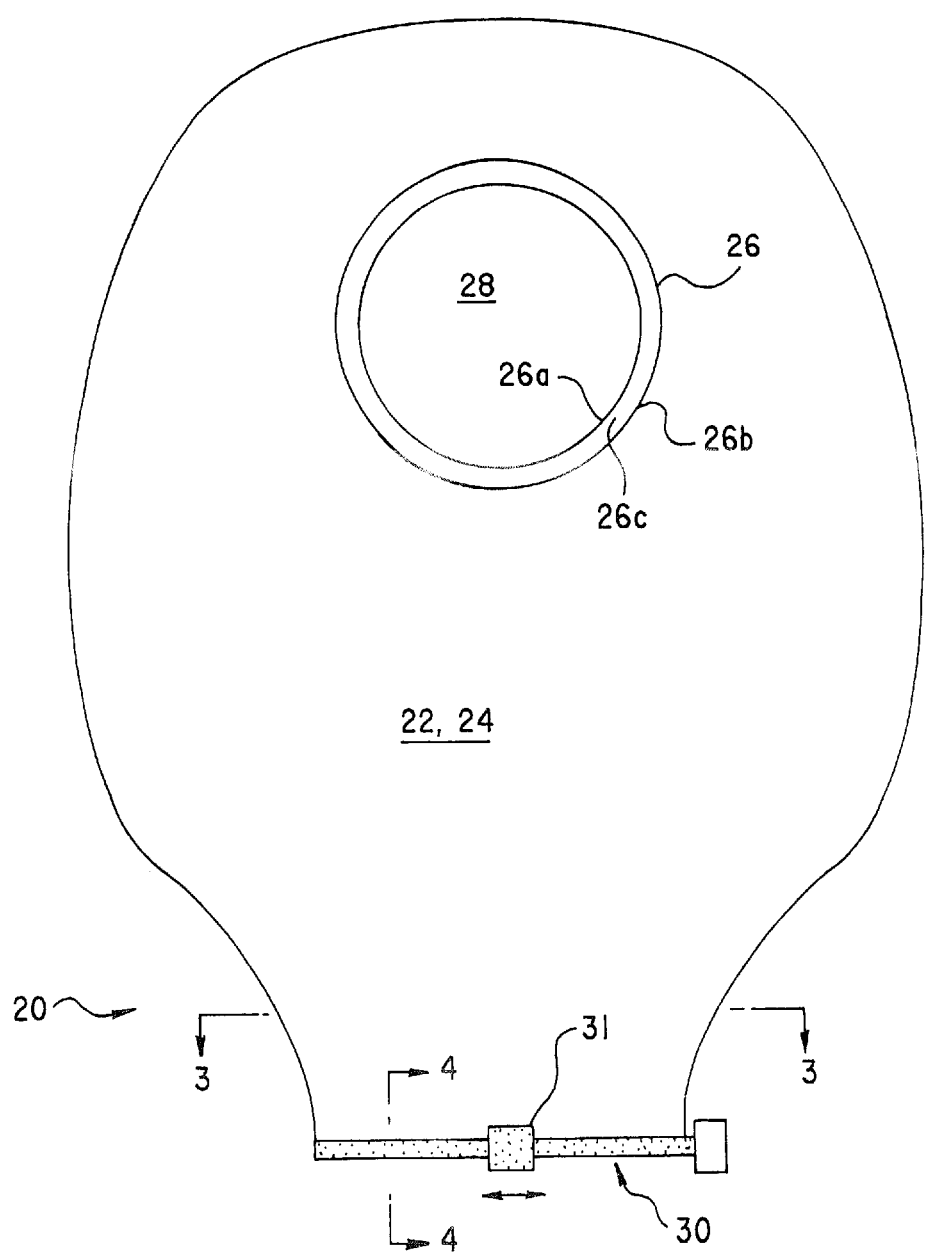
FIG. 2B is the ostomy pouch with the integral closure having the sealing mechanism according to an alternate embodiment of this invention.
Figure 4A:
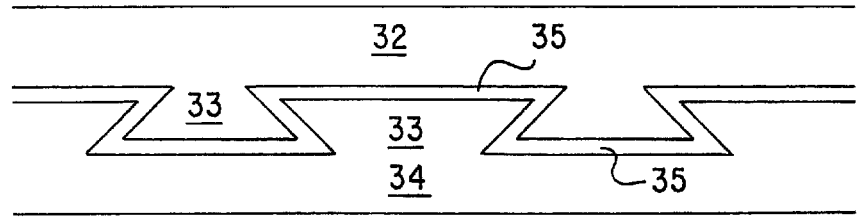
FIGS. 4A–4D are cross-section views of the different configurations of the male and female portions of the integral closure.
Figure 4B:
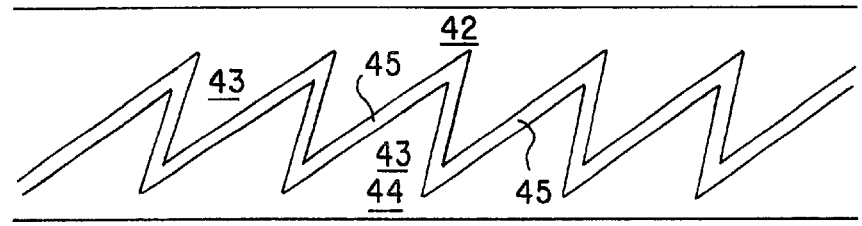
Figure 4C:
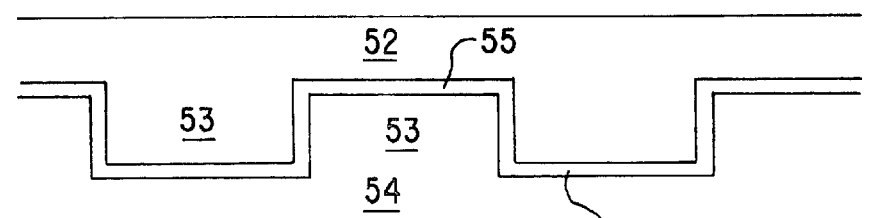
Figure 4D:
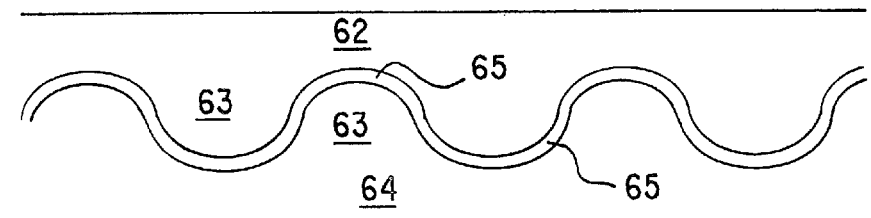

The ostomy pouch 20, as shown in FIGS. 2A–B, comprises first and second wall panels 22 and 24 that are connected along the top and both sides of the pouch 20. The connected wall panels 22 and 24 form a storage area 23 within which the contents expelled from the stoma are stored. See FIG. 3A. The first and second wall panels 22 and 24 are formed from a plastic or other such reusable, gas and liquid impermeable material. Such materials include, but are not limited to, a polymer, such as polyethylene, copolymer of vinyl chloride, and polyvinylidene chloride; and laminates, such as ethylene vinylacetate or polyvinylidene chloride, wherein the polymeric material may be either clear or opaque.

More example of the gas and liquid permeable materials include, a low density polyethylene, linear low density polyethylene, substantially linear copolymers of ethylene and a C3–C8 α-olefin, polypropylene, polyvinyl chloride, mixtures of two or more of the above-listed polymers, or mixtures with one or more of the above-listed polymers with another thermoplastic polymer Another example of a gas and liquid impermeable material includes a polyolefin film laminated with an appropriate barrier material, such as a low density polyethylene coextruded with a layer of polyvinylidene chloride.

The thickness of such liquid and gas impermeable liquid materials will vary depending on the particular polymeric material used, but is usually in the range of approximately 2 to 8 mils.

Figure 3B:
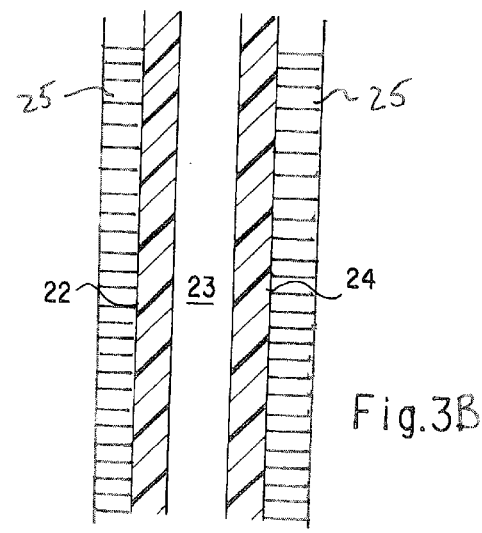
FIG. 3B is a cross-sectional view of an alternate embodiment of the ostomy pouch shown in FIGS. 2A and 2B.

Also, as shown in FIG. 3B, the outer surfaces of one or both of the first and second wall panels 22 and 24 may be provided with a relatively soft fabric covering layer 25 to enhance wearer comfort and prevent the outer surfaces of the first and second wall panels 22 and 24 from adhering to the skin or clothing of the ostomate. Such a soft covering layer 25 may be formed from a soft, non-woven thermoplastic material or a woven material, such, for example, cotton.

The ostomy pouch 20 also includes a locking ring 26 having an opening 28 formed therein. The locking ring 26 is designed to receive the locking ring 16 on the wafer 10 so that the wafer 10 and ostomy pouch 20 can be locked together. In particular, the locking ring 26 may include an interior raised edge 26*a* and an exterior raised edge 26*b* with a channel 26*c* formed therebetween.

To secure the locking ring 16 of the wafer 10 in the locking ring 26 of the ostomy pouch 20, the locking ring 16 of the wafer 10 is positioned so the raised portion of the locking ring 16 snaps into the channel 26*c* and is securely held therein by the interior and exterior edges 26*a* and 26*b*. As such, the stoma opening 18 of the wafer 10 is in communication with the opening 28 of the ostomy pouch 20. Accordingly, the contents of the intestine, i.e., fecal matter, that are expelled by the stoma pass through the stoma opening 18 and are conveyed to the storage area 23 of the ostomy pouch 20 where they are kept until the ostomate disposes of such as will be explained in further detail below.

A bottom opening 29 (FIG. 6B) of the ostomy pouch 20 is formed by the wall panels 22 and 24 not being connected at the bottom portion of the pouch 20. The bottom opening 29 is sealed by a closure 30 that is integral with the ostomy pouch 20. As shown in FIGS. 4A–4D, the wall panel 22 at the bottom portion of the ostomy pouch 20 includes a first portion 32, 42, 52, and 62, whereas the wall panel 24, also at the bottom portion of the ostomy pouch 20 and opposite the wall panel 22, includes a second portion 34, 44, 54, and 64. The first and second portions 32, 42, 52, 62 and 34, 44, 54, 64, respectively, are formed from a material that is different than and more rigid than the material from which the wall panels 22 and 24 of the ostomy pouch 20 are formed. As such, when the first and second portions 34, 44, 54, 65 and 32, 42, 52, 62 are sealed together, the closures can withstand the pressure of the contents of the ostomy pouch and not break the closure seal.

Furthermore, the first portions 32, 42, 52, 62 and second portions 34, 44, 54, 64 each include male projections 33, 43, 53, and 63 and corresponding female slots 35, 45, 55, and 65. The male projections 33, 43, 53, and 63 and female slots 35, 45, 55, and 65 are alternately arranged along the first and second portions 32, 42, 52, 62 and 34, 44, 54, and 64, respectively, from side to side so that the male projections 33, 43, 53, and 63 can manually be pressed by the fingertips of the ostomate into the female slots 35, 45, 55, and 65 as shown in FIGS. 4A–4D.

FIGS. 4A–4D show the male projections 33, 43, 53, and 63 and the corresponding female slots 35, 45, 55, and 65 as being trapezoidal, triangular, rectangular, and curvilinear in shape, respectively. However, the above-described and illustrated shapes are merely exemplary and it is within the scope of this invention to have the male projections and female slots be any suitable geometric configuration.

Figure 5:
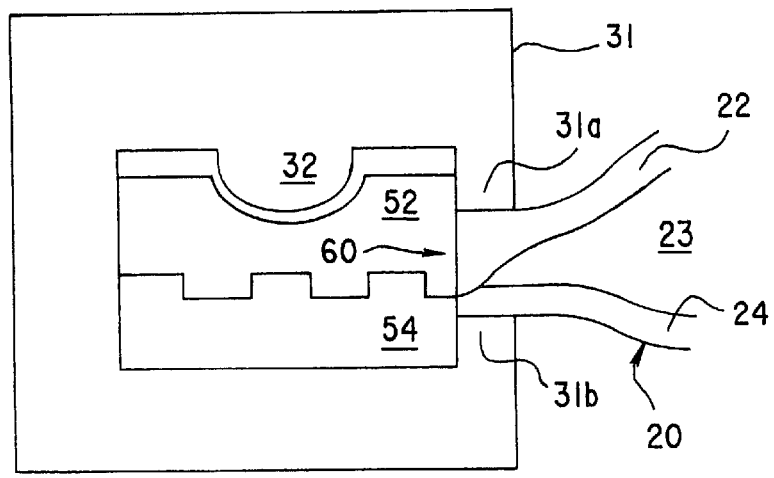
FIG. 5 is a schematic diagram illustrating how the slider matingly locks the male and female portions of the integral closure.

Additionally, in an alternate embodiment of this invention, as shown in FIG. 2B, the integral closure system may further include a slider mechanism 31 to facilitate sealing of the first and second portions 32, 42, 52, 62 and 34, 44, 54, 64, respectively. As shown in FIG. 5, the slider mechanism 31 is configured to receive the first and second portions 52 and 54 of the wall panels 22 and 24, respectively, of the ostomy pouch 20. The rectangular shaped projections and slots 52 and 54 are shown merely for example to provide an understanding of the operation of the slider mechanism 31.

The slider mechanism 31 is generally rectangular in shape with an opening 60 formed in one side to receive the first and second portions 52 and 52 of the wall panels 22 and 24, respectively. The slider mechanism 31 also includes pinching members 31*a* and 31*b* that form the opening 60 and apply pressure to the wall panels 22 and 24 of the ostomy pouch 20 so as to apply pressure thereto and prevent the bottom opening 29 of the ostomy pouch 20 from unintentionally releasing the contents in the storage area 23.

Furthermore, the slider mechanism 31 includes a finger 32 extending into an internal cavity of the slider mechanism 31. The cavity is configured to receive the first and second portions 52 and 54 of the wall panels 22 and 24, respectively. The finger 32 applies pressure to at least one of the first and second portions 52 and 54 so as to force the projections 53 to matingly lock with the slots 55 to form an air-tight, odor free seal. Like the first portions 32, 42, 52, and 62 and second portions 34, 44, 54, and 64 discussed above, the slider mechanism 31 of the integral closure 30 is formed from a material that is different from and more rigid than the material from which the first and second wall panels 22 and 24 are formed.

The more rigid material of the integral closure 30 increases the lock strength of the integral closure 30 because such materials typically do not give as easily as the relatively less rigid or more flexible materials from which the first and second wall panels 22 and 24 are formed, thereby making it more difficult for the integral closure 30 to disengage from a locked state and preventing the unintentional discharge of the ostomy pouch 20 contents.

Examples of such more rigid materials are, but not limited to, nylon, polypropylene, polystyrene, acetal, toughened acetal, polyketone, polybutylene terephthalene, high density polyethylene, polycarbonate, or ABS. Furthermore, the first portion, the second portion, as well as the slider, can be manufactured using any well known method, such as, for example, blow or cast extrusion, as well as injection molding.

It should be noted that while several exemplary materials have been provided herein for manufacturing the first and second wall panel 22 and 42, the first portion 32, 42, 52, and 62 of the integral closure 30, the second portion 34, 44, 54, and 64 of the integral closure 30, and the slider mechanism 31, such materials are merely provided for exemplary purposes as it is well known in the art to use such materials, as well as other well known and suitable materials, in ostomy appliances. Rather, it is important that the material chosen for manufacturing the integral closure 30 is different from and more rigid than the material chosen to manufacture the first and second wall panels 22 and 24 of the ostomy pouch 20. Also, the material chosen to manufacture the integral closure 30 must be compatible with the material ultimately chosen to manufacture the ostomy pouch 20. Furthermore, the material selected to manufacture the integral closure 30 must selected such that the integral closure 30 is integratable within the ostomy pouch 20.

Figure 6A:
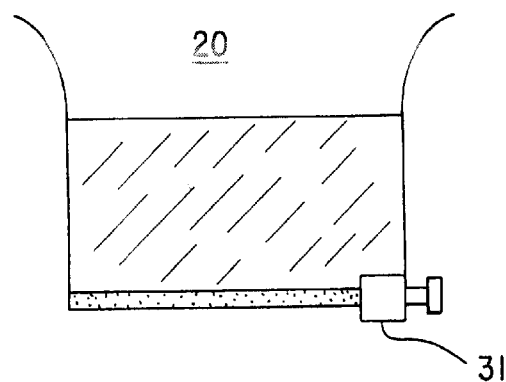
FIGS. 6A–6B illustrate the closed and opened states of the integral closure.
Figure 6B:
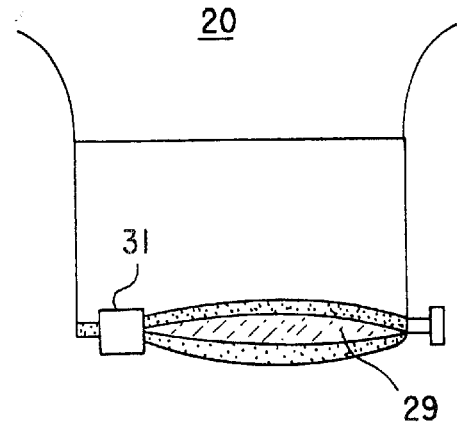

As shown in FIG. 6A, when the slider mechanism 31 is slid along the bottom of the ostomy pouch 20, the projections and slots 53 and 55 mate, thereby providing the desired seal and closes the ostomy pouch 20. The slider mechanism, 31 as well as the manual application of pressure to the mating components, precludes the ostomate from the cumbersome and complicated techniques necessary in the prior art. Quite simply, as described above, the ostomate merely needs to either manually apply pressure to or slide the slider mechanism 31 along the bottom of the pouch 20 to close the bottom opening 29. To open the bottom opening 29 to discard the stored contents, the ostomate merely opens the bottom opening 29 with their fingers or slides the slider mechanism 31 in the reverse direction and manually separates the mated first and second portions. See FIG. 6B.

As such, the above-described ostomy appliance provides a reusable, resealable ostomy pouch having an integral closure that can be emptied without being detached from the abdomen of the ostomate, and without the need of a separate clamp, or separate securing device. The ostomy appliance of this invention is secure, easy to manufacture, convenient, clean, and easy-to-use. Furthermore, the ostomy appliance overcomes many of the previously described drawbacks of the currently used devices and techniques and does not require a substantial amount of dexterity on the part of the ostomate. Additionally, because the closure is integral with the ostomy pouch, the ostomate need not worry about the closing device gauging the ostomate or otherwise seriously injuring the user or coming in contact with the fecal matter.

While the invention has been described in conjunction with specific embodiments thereof, it is evident that many alternatives, modifications and variations may be apparent to those skilled in the art. Accordingly, the specific embodiments of the invention as set forth herein are intended to be illustrative, not limiting. As such, various changes may be made without departing from the spirit and scope of the invention as set forth in the following claims.

What is claimed:

1. An ostomy appliance that collects excreted human body waste, comprising:

a wafer having a stoma opening through which the excreted human body waste passes;

an ostomy pouch having first and second wall panels connected along a top edge and both side edges of the ostomy pouch to form a storage area therebetween, the first wall panel having an opening that communicates with the stoma opening, wherein the excreted human body waste passing through the stoma opening of the wafer is stored in the storage area, the first and second wall panels form a bottom opening at a bottom edge of the ostomy pouch through which the human body waste is disposed; and a closure integral with the bottom opening of the ostomy pouch and including a first portion of the first wall panel at the bottom opening of the ostomy pouch and a second portion of the second wall panel at the bottom opening of the ostomy pouch, wherein the first and second portions of the integral closure matingly engage each other to form an air-tight, odor-free seal that encloses the ostomy pouch with the human body waste being stored in the storage area, wherein the first and second portions are formed from a first material different and more rigid than a second material from which the first and second wall panels are formed, wherein the sealed integral closure withstands a pressure applied to the integral closure by the human body waste stored in the storage area, wherein the first and second portions each include alternating and interlocking male projections and female slots.

2. The ostomy appliance according to claim 1, wherein the alternating and interlocking male projections and female slots have a shape that is one of trapezoidal, triangular, rectangular, and curvilinear.

3. The ostomy appliance according to claim 1, wherein the wafer and ostomy pouch are integrated to form a one piece appliance.

4. The ostomy appliance according to claim 1, wherein the first and second wall panels of the ostomy pouch are manufactured from a gas and liquid impermeable polymeric material.

5. The ostomy appliance according to claim 4, wherein the polymeric material is at least one of polyethylene, copolymer of vinyl chloride, polyvinylidene chloride, low density polyethylene, linear low density polyethylene, linear copolymers of ethylene, C3–C8 α-olefin, polypropylene, polyvinyl chloride.

6. The ostomy appliance according to claim 4, wherein the polymeric material is one of clear and opaque.

7. The ostomy appliance according to claim 4, wherein a laminate is applied to an outer surface of the polymeric material.

8. The ostomy appliance according to claim 7, wherein the laminate is one of ethylene vinylacetate and polyvinylidene chloride.

9. The ostomy appliance according to claim 4, wherein the polymeric material has thickness in a range of 2 to 8 mils.

10. The ostomy appliance according to claim 1, wherein an outer surface of the first and second wall panels is provided with a fabric covering layer.

11. The ostomy appliance according to claim 1, wherein the first and second portions are manufactured from one of nylon, polypropylene, polystyrene, acetal, toughened acetal, polyketone, polybutylene terephthalene, high density polyethylene, and polycarbonate.

12. The ostomy appliance according to claim 4, further comprising a slider that receives and substantially encompasses the first and second portions of the integral closure.

13. The ostomy appliance according to claim 12, wherein the slider comprises an internal cavity and first and second pinching members that form an opening through which the ostomy pouch is received and apply a pressure to the first and second wall panels to prevent the bottom opening from opening and unintentionally releasing the stored human body waste.

14. The ostomy appliance according to claim 13, wherein the slider further comprises a finger extending inward into the internal cavity, wherein the finger applies pressure to at least one of the first and second portions to force the male projections to matingly interlock with the female slots.

15. The ostomy appliance according to claim 12, wherein the slider is manufactured from one of nylon, polypropylene, polystyrene, acetal, toughened acetal, polyketone, polybutylene terephthalene, high density polyethylene, and polycarbonate.

16. The ostomy appliance according to claim 15, wherein the first portion, second portion, and slider are manufactured from one of blow extrusion, cast extrusion, and injection molding.

17. An ostomy appliance that collects excreted human body waste, comprising:

a wafer having a stoma opening through which the excreted human body waste passes;

an ostomy pouch having first and second wall panels connected along a top edge and both side edges of the ostomy pouch to form a storage area therebetween, the first wall panel having an opening that communicates with the stoma opening, wherein the excreted human body waste passing through the stoma opening of the wafer is stored in the storage area, the first and second wall panels form a bottom opening at a bottom edge of the ostomy pouch through which the human body waste is disposed; and a closure integral with the bottom opening of the ostomy pouch and including a first portion of the first wall panel at the bottom opening of the ostomy pouch and a second portion of the second wall panel at the bottom opening of the ostomy pouch, wherein the first and second portions of the integral closure matingly engage each other to form an air-tight, odor-free seal that encloses the ostomy pouch with the human body waste being stored in the storage area;

a slider that receives and substantially encompasses the first and second portions of the integral closure, wherein the slider comprises an internal cavity and first and second pinching members that form an opening through which the ostomy pouch is received and apply a pressure to the first and second wall panels to prevent the bottom opening from opening and unintentionally releasing the stored human body waste, wherein the first and second portions are formed from a first material different and more rigid than a second material from which the first and second wall panels are formed, wherein the sealed integral closure withstands a pressure applied to the integral closure by the human body waste stored in the storage area, wherein the first and second portions each include alternating and interlocking male projections and female slots.

18. The ostomy appliance according to claim 17, wherein the alternating and interlocking male projections and female slots have a shape that is one of trapezoidal, triangular, rectangular, and curvilinear.

19. The ostomy appliance according to claim 17, wherein the wafer and ostomy pouch are integrated to form a one piece appliance.

20. The ostomy appliance according to claim 17, wherein the slider further comprises a finger extending inward into the internal cavity, wherein the finger applies pressure to at least one of the first and second portions to force the male projections to matingly interlock with the female slots.

21. The ostomy appliance according to claim 17, wherein the first and second wall panels of the ostomy pouch are manufactured from a gas and liquid impermeable polymeric material.

22. The ostomy appliance according to claim 21, wherein the polymeric material is at least one of polyethylene, copolymer of vinyl chloride, polyvinylidene chloride, low density polyethylene, linear low density polyethylene, linear copolymers of ethylene, C3–C8 α-olefin, polypropylene, polyvinyl chloride.

23. The ostomy appliance according to claim 21, wherein the polymeric material is one of clear and opaque.

24. The ostomy appliance according to claim 21, wherein a laminate is applied to an outer surface of the polymeric material.

25. The ostomy appliance according to claim 24, wherein the laminate is one of ethylene vinylacetate and polyvinylidene chloride.

26. The ostomy appliance according to claim 21, wherein the polymeric material has thickness in a range of 2 to 8 mils.

27. The ostomy appliance according to claim 17, wherein an outer surface of the first and second wall panels is provided with a fabric covering layer.

28. The ostomy appliance according to claim 17, wherein the first and second portions are manufactured from one of nylon, polypropylene, polystyrene, acetal, toughened acetal, polyketone, polybutylene terephthalene, high density polyethylene, and polycarbonate.

29. The ostomy appliance according to claim 17, wherein the slider further comprises a finger extending inward into the internal cavity, wherein the finger applies pressure to at least one of the first and second portions to force the male projections to matingly interlock with the female slots.

30. The ostomy appliance according to claim 17, wherein the slider is manufactured from one of nylon, polypropylene, polystyrene, acetal, toughened acetal, polyketone, polybutylene terephthalene, high density polyethylene, and polycarbonate.

31. The ostomy appliance according to claim 17, wherein the first portion, second portion, and slider are manufactured from one of blow extrusion, cast extrusion, and injection molding.

* * * * *